(12) United States Patent
Curello et al.

(10) Patent No.: US 7,642,742 B2
(45) Date of Patent: Jan. 5, 2010

(54) FUEL CELL SYSTEM WITH FUEL SUPPLY MONITORING SYSTEM AND METHOD OF USE

(75) Inventors: Andrew J. Curello, Hamden, CT (US); Charles Loonis, Milford, CT (US); Hung T. Than, Rockville, MD (US)

(73) Assignee: Societe BIC (FR)

(*) Notice: Subject to any disclaimer, the term of this patent is extended or adjusted under 35 U.S.C. 154(b) by 459 days.

(21) Appl. No.: 11/196,685

(22) Filed: Aug. 2, 2005

(65) Prior Publication Data

US 2006/0019135 A1 Jan. 26, 2006

Related U.S. Application Data

(63) Continuation-in-part of application No. 10/725,235, filed on Dec. 1, 2003, now Pat. No. 7,329,348, which is a continuation-in-part of application No. 10/725,236, filed on Dec. 1, 2003, now Pat. No. 7,117,732, which is a continuation-in-part of application No. 10/728,237, filed on Dec. 1, 2003.

(51) Int. Cl.
*H01M 10/46* (2006.01)

(52) U.S. Cl. ..................... 320/101

(58) Field of Classification Search .......... 320/101, 320/116, 150; 429/12, 19, 20, 21
See application file for complete search history.

(56) References Cited

U.S. PATENT DOCUMENTS

| | | | |
|---|---|---|---|
| 4,261,956 A | 4/1981 | Adlhart | |
| 4,368,981 A | 1/1983 | Ozeki | |
| 5,945,231 A | 8/1999 | Narayanan et al. | |
| 5,992,008 A | 11/1999 | Kindler | |
| 6,254,748 B1 | 7/2001 | Surampudi et al. | |
| 6,306,285 B1 | 10/2001 | Narayanan et al. | |
| 6,428,918 B1 * | 8/2002 | Fuglevand et al. | 429/13 |
| 6,429,242 B1 | 8/2002 | Macher et al. | |
| 6,554,877 B2 | 4/2003 | Finkelshtain et al. | |
| 6,562,497 B2 | 5/2003 | Finkelshtain et al. | |
| 6,584,825 B2 | 7/2003 | Pratt et al. | |
| 6,589,679 B1 | 7/2003 | Acker et al. | |
| 6,758,871 B2 | 7/2004 | Finkelshtain et al. | |
| 6,773,470 B2 | 8/2004 | Finkelshtain et al. | |
| 6,815,101 B2 | 11/2004 | de Vaal et al. | |
| 6,828,049 B2 | 12/2004 | Bullock et al. | |

(Continued)

*Primary Examiner*—Edward Tso
(74) *Attorney, Agent, or Firm*—The H.T. Than Law Group

(57) ABSTRACT

A fuel cell includes a removable and replaceable fuel supply having fuel disposed therein. A system for monitoring various parameters of the fuel such as temperature, pressure, and the levels of dissolved oxygen is provided. A plurality of sensors is disposed on the fuel supply side that is capable of communicating with a controller and memory on the fuel cell side. In another embodiment, at least one sensor for measuring a system parameter of the fuel communicates with an RFID tag either remotely or via a hardwired link. The sensor and/or the RFID tag may be coated with a substance impervious to the caustic fuel. An RFID reader station collects the data. The controller may be included to use the data in real time to alter system parameters, such as fuel pumping rates or a bleed off, or to trigger a signal, such as to notify a user of an empty fuel supply.

41 Claims, 6 Drawing Sheets

U.S. PATENT DOCUMENTS

| | | |
|---|---|---|
| 2002/0076602 A1 | 6/2002 | Finkelshtain et al. |
| 2002/0154815 A1 | 10/2002 | Mitutani |
| 2003/0077491 A1 | 4/2003 | Lillis |
| 2003/0077493 A1 | 4/2003 | Colborn et al. |
| 2003/0082427 A1 | 5/2003 | Prasad et al. |
| 2003/0091883 A1 | 5/2003 | Peled et al. |
| 2003/0096150 A1 | 5/2003 | Rice et al. |
| 2003/0118881 A1 | 6/2003 | Walsh et al. |
| 2003/0129464 A1 | 7/2003 | Becerra et al. |
| 2003/0131663 A1 | 7/2003 | Gore et al. |
| 2003/0134162 A1 | 7/2003 | Gore et al. |
| 2003/0141188 A1 | 7/2003 | Imamura et al. |
| 2003/0150655 A1 | 8/2003 | Itou |
| 2003/0215681 A1 | 11/2003 | Appt et al. |
| 2004/0076860 A1 * | 4/2004 | Aso .......................... 429/23 |
| 2004/0175598 A1 | 9/2004 | Bliven et al. |
| 2004/0185316 A1 | 9/2004 | Wells et al. |
| 2006/0008687 A1 * | 1/2006 | Kaye et al. .................... 429/17 |

\* cited by examiner

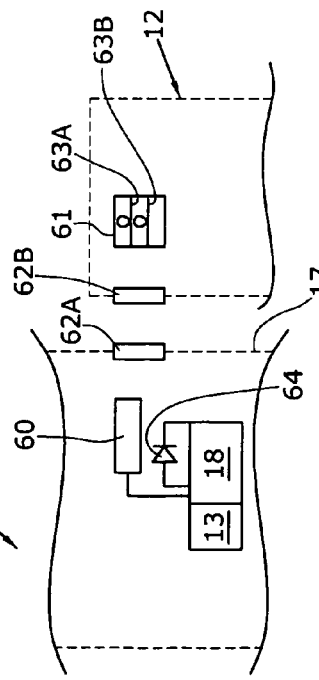
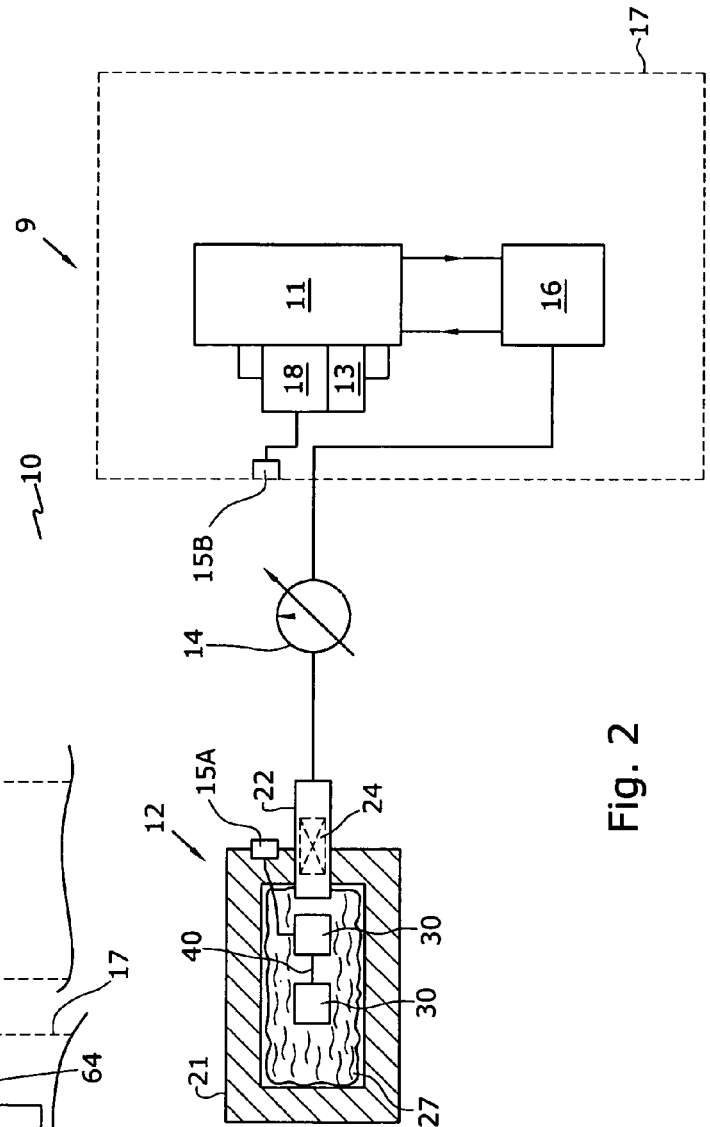
Fig. 1A
Fig. 2

FUEL CELL SYSTEM WITH FUEL SUPPLY MONITORING SYSTEM AND METHOD OF USE

CROSS-REFERENCE TO RELATED APPLICATIONS

This application is a continuation-in-part of commonly owned, U.S. application Ser. No. 10/725,235 now U.S. Pat. No. 7,329,348, Ser. No. 10/725,236 now U.S. Pat. No. 7,117,732 and Ser. No. 10/725,237, all of which were filed on Dec. 1, 2003, the disclosures of which are incorporated herein by reference.

FIELD OF THE INVENTION

The invention relates generally to fuel cells and monitoring technologies. In particular, sensor arrays linked to a remote control system and information storage device are used to monitor system parameters in a fuel cell.

BACKGROUND OF THE INVENTION

Fuel cells are devices that directly convert chemical energy of reactants, i.e., fuel and oxidant, into direct current (DC) electricity. For an increasing number of applications, fuel cells are more efficient than conventional power generation, such as combustion of fossil fuel, as well as portable power storage, such as lithium-ion batteries.

In general, fuel cell technology includes a variety of different fuel cells, such as alkali fuel cells, polymer electrolyte fuel cells, phosphoric acid fuel cells, molten carbonate fuel cells, solid oxide fuel cells and enzyme fuel cells. Today's more important fuel cells can be divided into several general categories, namely: (i) fuel cells utilizing compressed hydrogen ($H_2$) as fuel; (ii) proton exchange membrane (PEM) fuel cells that use alcohols, e.g., methanol ($CH_3OH$), metal hydrides, e.g., sodium borohydride ($NaBH_4$), hydrocarbons, or other fuels reformed into hydrogen fuel; (iii) PEM fuel cells that can consume non-hydrogen fuel directly or direct oxidation fuel cells; and (iv) solid oxide fuel cells (SOFC) that directly convert hydrocarbon fuels to electricity at high temperature.

Compressed hydrogen is generally kept under high pressure and is therefore difficult to handle. Furthermore, large storage tanks are typically required and cannot be made sufficiently small for consumer electronic devices. Conventional reformat fuel cells require reformers and other vaporization and auxiliary systems to convert fuels to hydrogen to react with oxidant in the fuel cell. Recent advances make reformer or reformat fuel cells promising for consumer electronic devices. The most common direct oxidation fuel cells are direct methanol fuel cells or DMFC. Other direct oxidation fuel cells include direct ethanol fuel cells and direct tetramethyl orthocarbonate fuel cells. DMFC, in which methanol is reacted directly with oxidant in the fuel cell, has promising power application for consumer electronic devices. SOFC convert hydrocarbon fuels, such as butane, at high heat to produce electricity. SOFC requires relatively high temperature in the range of 1000° C. for the fuel cell reaction to occur.

The chemical reactions that produce electricity are different for each type of fuel cell. For DMFC, the chemical-electrical reaction at each electrode and the overall reaction for a direct methanol fuel cell are described as follows:

Half-reaction at the anode:

$$CH_3OH + H_2O \rightarrow CO_2 + 6H^+ + 6e^-$$

Half-reaction at the cathode:

$$1.5O_2 + 6H^+ + 6e^- \rightarrow 3H_2O$$

The overall fuel cell reaction:

$$CH_3OH + 1.5O_2 \rightarrow CO_2 + 2H_2O$$

Due to both the migration of the hydrogen ions ($H^+$) through the PEM from the anode to the cathode and the inability of the free electrons ($e^-$) to pass through the PEM, the electrons flow through an external circuit, thereby producing an electrical current. The external circuit may be used to power many useful consumer electronic devices, such as mobile or cell phones, calculators, personal digital assistants, laptop computers, and power tools, among others.

DMFC is discussed in U.S. Pat. Nos. 5,992,008 and 5,945,231, which are incorporated herein by reference in their entireties. Generally, the PEM is made from a polymer, such as Nafion® available from DuPont, which is a perfluorinated sulfonic acid polymer having a thickness in the range of about 0.05 mm to about 0.5 mm, or other suitable membranes. The anode is typically made from a Teflonized carbon paper support with a thin layer of catalyst, such as platinum-ruthenium, deposited thereon. The cathode is typically a gas diffusion electrode in which platinum particles are bonded to one side of the membrane.

In another direct oxidation fuel cell, borohydride fuel cell (DBFC) reacts as follows:

Half-reaction at the anode:

$$BH_4^- + 8OH^- \rightarrow BO_2^- + 6H_2O + 8e^-$$

Half-reaction at the cathode:

$$2O_2 + 4H_2O + 8e^- \rightarrow 8OH^-$$

In a chemical metal hydride fuel cell, generally aqueous sodium borohydride is reformed and reacts as follows:

$$NaBH_4 + 2H_2O \rightarrow (\text{heat or catalyst}) \rightarrow 4(H_2) + (NaBO_2)$$

Half-reaction at the anode:

$$H_2 \rightarrow 2H^+ + 2e^-$$

Half-reaction at the cathode:

$$2(2H^+ + 2e^-) + O_2 \rightarrow 2H_2O$$

Suitable catalysts for this reaction include platinum and ruthenium, as well as other metals. The hydrogen fuel produced from reforming sodium borohydride is reacted in the fuel cell with an oxidant, such as $O_2$, to create electricity (or a flow of electrons) and water byproduct. A sodium borate ($NaBO_2$) byproduct is also produced by this process. A sodium borohydride fuel cell is discussed in U.S. Pat. No. 4,261,956, which is incorporated herein by reference. Therefore, the known chemical hydride reactions that use aqueous metal hydride have about 9 to 12 weight percentage storage expectancy, and the liquid and the catalyst used in the wet chemical reaction system need to be closely monitored. Additionally, it is difficult to maintain the stability of a metal hydride solution over a long period of time, because according to the formula $t\frac{1}{2} = pH^* \log(0.034 + kT)$, which provides the half life of the reaction, the reaction of hydrolysis always occurs very slowly. Furthermore, if the solution is stabilized, the reactivity is not complete.

In a hydride storage method, the reaction is as follows:

$$Metal + H_2 \rightarrow hydride + heat$$

However, storage expectancy of such a reaction is only about 5 weight percentage. Additionally, such reactions can be expensive and difficult to package.

Another known method to produce hydrogen is a dry hydride reaction. Dry reaction, generally, involves the following reaction:

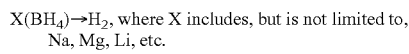
$X(BH_4) \rightarrow H_2$, where X includes, but is not limited to, Na, Mg, Li, etc.

Again, dry reactions have several disadvantages, such as having a storage expectancy of only about 10 weight percentage, and the need to closely monitor the pressure.

An additional method to produce hydrogen gas is by a pressure storage method using the formula $PV=nRT$, wherein P is pressure, V is volume, n is a number of moles, R is the gas constant, and T is temperature. This method requires constant pressure monitoring.

One of the most important features for fuel cell application is fuel storage. Another important feature is regulating the transport of fuel out of the fuel cartridge to the fuel cell. To be commercially useful, fuel cells such as DMFC or PEM systems should have the capability of storing sufficient fuel to satisfy the consumers' normal usage. For example, for mobile or cell phones, for notebook computers, and for personal digital assistants (PDAs), fuel cells need to power these devices for at least as long as the current batteries and, preferably, much longer. Additionally, the fuel cells should have easily replaceable or refillable fuel tanks to minimize or obviate the need for lengthy recharges required by today's rechargeable batteries.

In the operation of a fuel cell, monitoring various system parameters in real time is highly desirable for a number of reasons. First, tracking the fuel usage history indicates the amount of fuel remaining in the fuel supply and provides the user with information regarding the remaining useful life of the fuel supply. The patent literature discloses a number of containers for consumable substances that include electronic memory components. U.S. patent application publication no. US 2002/0154815, which is incorporated herein in its entirety by reference, discloses a variety of containers that may include read-only memories, programmable read-only memories, electronically erasable programmable read-only memories, non-volatile random access memories, volatile random access memories or other types of electronic memory. These electronic memory devices may be used to retain coded recycle, refurbishing and/or refilling instructions for the containers, as well as a record of the use of the containers. The containers may comprise liquid ink or powdered toner for a printer. Alternatively, the containers or fuel supply may comprise a fuel cell or a fuel supply therefor.

Also, the transfer of the fuel from the fuel supply to the fuel cell may depend upon, inter alia, the viscosity of the fuel. For example, the viscosity of methanol, which is about $8.17 \times 10^{-4}$ Pa-s at 1 atmosphere and 0° C., drops to about $4.5 \times 10^{-4}$ Pa-s at 1 atmosphere and 40° C., representing about a 50% reduction. If the system is able to detect in real time the temperature and/or pressure of the fuel contained within the fuel supply, then the fuel cell can self-regulate how long a fuel pump should run in order to provide an appropriate amount of fuel. As fuel is supplied at the optimum rate, the efficiency of the system is increased. Also, monitoring the pressure of the fuel within the fuel supply can alert the user or the system of unacceptable high or unacceptable low pressure levels. Furthermore, the usable life of the fuel cell can be increased if exposure to fuel is limited to the amount of fuel necessary for operation. In other words, flooding the fuel cell with excess fuel may damage the fuel cell.

One option among others for a monitoring system is using a radio frequency identification (RFID) system. Systems using RFID technologies are well known, particularly for uses such as tracking inventory such as library or retail store inventory, automated payment systems such as passes for toll booths, and security systems such as smart keys for starting a car. Such systems may be large and active systems, utilizing battery-powered transceiver circuitry. Such systems may also be very small and passive, in which a transponder receives power from the base station or reader only when information is desired to be transmitted or exchanged.

A typical RFID system includes a reusable identifying device typically referred to as a tag, but sometimes designated as a "card," "key," or the like. The RFID system also requires a recognition or reader station that is prepared to recognize identifying devices of predetermined characteristics when such identifying device is brought within the proximity of the reader station. Typically, a reader station includes an antenna system that reads or interrogates the tags via a radio frequency (RF) link and a controller. The controller directs the interrogation of the tags and may provide memory for storing the data collected from the tags. Further, the controller may provide a user interface so that a user may externally monitor the data.

In operation, as a tag comes within sufficient proximity to an RFID reader station, the antenna emits RF signals towards the tag and the tag transmits responses to the antenna. The tags can be powered by an internal battery (an "active" tag) or by inductive coupling receiving induced power from the RF signals emitted from the antenna (a "passive" tag). Inductive coupling takes place between the two devices when they are proximate to one another; physical contact is unnecessary. Passive tags have zero maintenance and virtually unlimited life. The life span of an active tag is, however, limited by the lifetime of the battery, although some tags offer replaceable batteries.

Current monitoring systems with RFID tags have not been adapted for use with fuel cell systems, either in terms of the type of data desired to be monitored or in terms of the ability of the system to withstand the harsh environment due to contact with fuel cell fuels. It would, therefore, be desirable to provide an RFID monitoring system and other types of monitoring systems for use with a fuel cell system.

SUMMARY OF THE INVENTION

Briefly, in accordance with one aspect of the present invention, a system for monitoring a fuel cell includes a fuel cell supply connected to a fuel cell. A plurality of sensors is operatively connected to the fuel supply. A controller is connected to the fuel cell and to an optional information storage device. A sensor communication link connects the plurality of sensors and the controller. A memory communication link connects the controller and the optional information storage device.

According to another aspect of the present invention, a fuel supply for a fuel cell includes a container having fuel disposed therewithin. A sensor for monitoring a condition of the fuel is located on or within the fuel supply. An RFID tag is configured to communicate with the sensor and adapted to be interrogated by an RFID reader station.

According to another aspect of the present invention, a method for monitoring a condition of fuel within a fuel cell comprises the steps of (1) providing a fuel cell connected to a fuel supply containing a fuel; (2) collecting data regarding the fuel using a plurality of sensors; (3) relaying the information from the sensor to a controller and optionally to an information storage device, wherein the plurality of sensors is located in or on the fuel supply and the information storage device is located remotely from the plurality of sensors.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 1a is a schematic view of an alternate embodiment of a fuel cell system according to the present invention incorporating passive optical sensors;

FIG. 2 is a schematic view of a fuel cell system according to the present invention, wherein a sensor array is connected to a remotely located controller and information storage device;

DETAILED DESCRIPTION OF THE PREFERRED EMBODIMENTS

Figure 1:
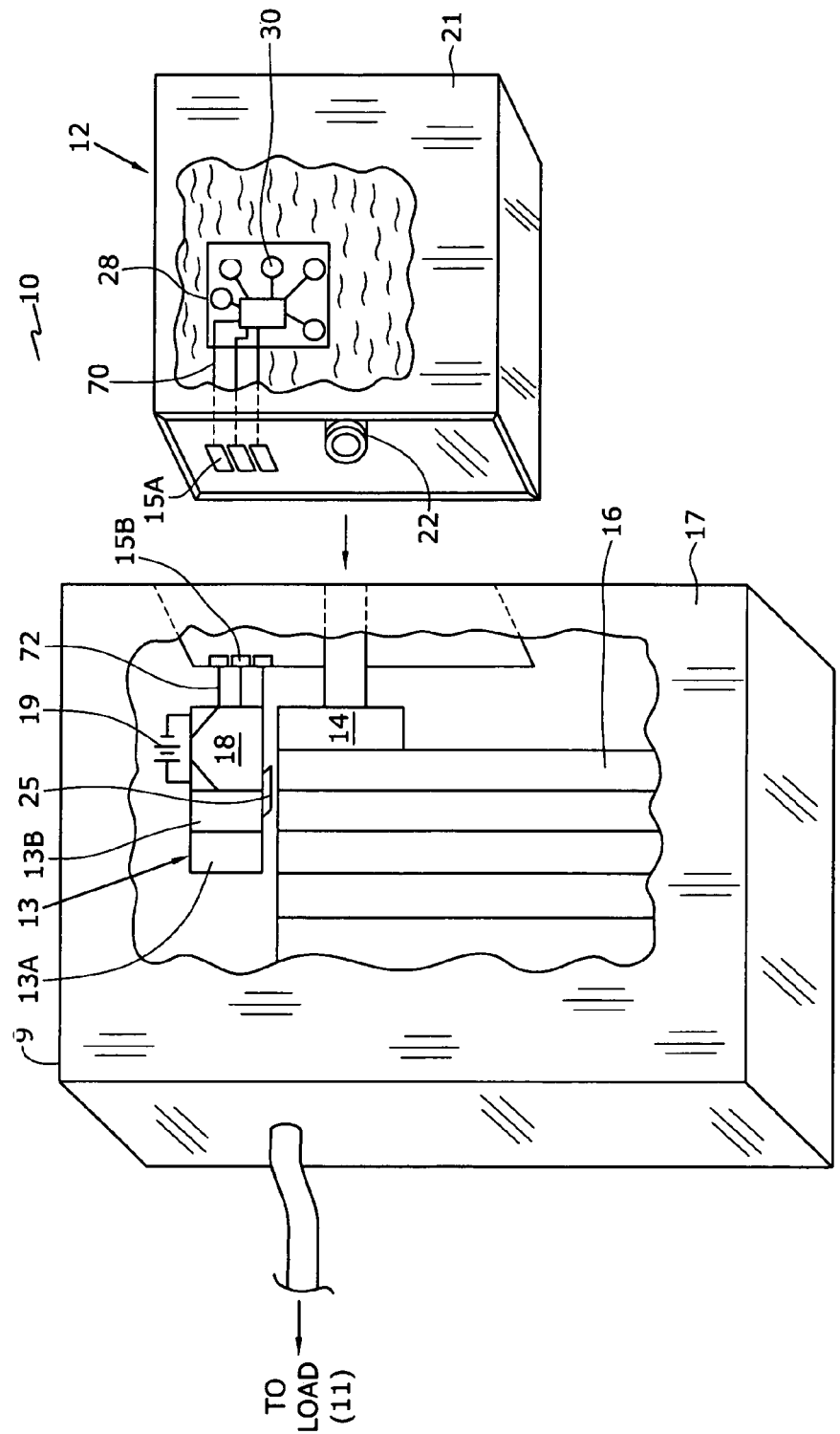
FIG. 1 is a perspective break-away view of a fuel cell system according to the present invention.

As illustrated in the accompanying drawings and discussed in detail below, the present invention is directed to a fuel supply, which stores fuel cell fuels such as methanol and water, methanol/water mixture, methanol/water mixtures of varying concentrations or pure methanol. Methanol is usable in many types of fuel cells, e.g., DMFC, enzyme fuel cell and reformat fuel cell, among others. The fuel supply may contain other types of fuel cell fuels, such as ethanol or other alcohols, chemicals that can be reformatted into hydrogen, or other chemicals that may improve the performance or efficiency of fuel cells. Fuels also include potassium hydroxide (KOH) electrolyte, which is usable with metal fuel cells or alkali fuel cells, and can be stored in fuel supplies. For metal fuel cells, fuel is in the form of fluid borne zinc particles immersed in a KOH electrolytic reaction solution, and the anodes within the cell cavities are particulate anodes formed of the zinc particles. KOH electrolytic solution is disclosed in United States published patent application no. 2003/0077493, entitled "Method of Using Fuel Cell System Configured to Provide Power to One or more Loads," published on Apr. 24, 2003, which is incorporated herein by reference in its entirety. Fuels also include a mixture of methanol, hydrogen peroxide and sulfuric acid, which flows past a catalyst formed on silicon chips to create a fuel cell reaction. Fuels also include a blend or mixture or methanol, sodium borohydride, an electrolyte and other compounds, such as those described in U.S. Pat. Nos. 6,554,877, 6,562,497 and 6,758,871, which are incorporated by reference in their entireties. Fuels also include those that are partially dissolved in solvent and partially suspended in solvent, described in U.S. Pat. No. 6,773,470 and those that include both liquid fuel and solid fuels, described in United States published patent application number 2002/076602. Both of these references are also incorporated by reference in their entireties.

Fuels also include metal hydrides, such as sodium borohydride ($NaBH_4$) and water, discussed above. Fuels further include hydrocarbon fuels, which include, but are not limited to, butane, kerosene, alcohol and natural gas, disclosed in United States published patent application no. 2003/0096150, entitled "Liquid Hereto-Interface Fuel Cell Device," published on May 22, 2003, which is incorporated herein by reference in its entirety. Fuels also include liquid oxidants that react with fuels. The present invention is, therefore, not limited to any type of fuels, electrolytic solutions, oxidant solutions or liquids or solids contained in the supply or otherwise used by the fuel cell system. The term "fuel" as used herein includes all fuels that can be reacted in fuel cells or in the fuel supply, and includes, but is not limited to, all of the above suitable fuels, electrolytic solutions, oxidant solutions, gasses, liquids, solids and/or chemicals and mixtures thereof.

As used herein, the term "fuel supply" includes, but is not limited to, disposable cartridges, refillable/reusable cartridges, containers, cartridges that reside inside the electronic device, removable cartridges, cartridges that are outside of the electronic device, fuel tanks, fuel reservoirs, fuel refilling tanks, other containers that store fuel and the tubings connected to the fuel tanks and containers. While a cartridge is described below in conjunction with the exemplary embodiments of the present invention, it is noted that these embodiments are also applicable to other fuel supplies and the present invention is not limited to any particular type of fuel supplies.

The fuel supply of the present invention can also be used to store fuels that are not used in fuel cells. These applications include, but are not limited to, storing hydrocarbons and hydrogen fuels for micro gas-turbine engines built on silicon chips, discussed in "Here Come the Microengines," published in The Industrial Physicist (December 2001/January 2002) at pp. 20-25. Other applications include storing traditional fuels for internal combustion engines; hydrocarbons, such as butane for pocket and utility lighters and liquid propane; as well as chemical fuels for use in personal portable heating devices. As used herein, the term "fuel cell" includes fuel cells as well as other machineries usable with the cartridges of the present invention.

As illustrated in the figures, the present invention is directed to a fuel cell system 10 for powering a load 11 (shown in FIGS. 2-5). Load 11 is typically an electronic device that fuel cell system 10 powers. Load or electrical device 11 is preferably the external circuitry and associated functions of any useful consumer electronic device, although load 11 may also have fuel cell system 10 integrated therewith. Examples of electronic device 11 include, but are not limited to, mobile or cell phones, calculators, power tools, gardening tools, personal digital assistants, digital cameras, laptop computers, computer games systems, portable music systems (MP3 or CD players), global positioning systems, and camping equipment, among others.

Referring to FIG. 1, the first embodiment of fuel cell system 10 includes a fuel cell 9 having a fuel cell housing 17 and a fuel supply 12 having a fuel supply housing 21. Also contained within fuel cell housing 17 is preferably a pump 14 for transferring fuel from fuel supply 12 to fuel cell units 16. Suitable pumps 14, including but not limited to piezo-electric pumps, are fully disclosed in the parent '237 application, and also in commonly owned, co-pending U.S. patent application Ser. No. 10/356,793; entitled "Fuel Cartridge for Fuel Cells," filed on Jan. 31, 2003, Ser. No. 10/629,004; entitled "Fuel Cartridge with Flexible Liner," filed on Jul. 29, 2003; and patent application Ser. No. 10/629,006, entitled "Fuel Cartridge with Connecting Valve," filed on Jul. 29, 2003. The disclosures of these references are incorporated herein by reference in their entireties. In another embodiment, fuel supply 12 is a pressurized fuel supply, which automatically controls the amount of fuel transferred to fuel cell 9 based upon the internal pressure of fuel supply 12 as discussed in the '004 application, among other references. As is described in commonly owned, co-pending U.S. application Ser. Nos. 10/679,756, entitled "Fuel Cartridges for Fuel Cells and Methods for Making Same," filed on Oct. 6, 2003; Ser. No. 11/067,167, entitled "Hydrogen Generating Fuel Cell Cartridges," filed on Feb. 25, 2005; and Ser. No. 11/066,573, entitled "Hydrogen Generating Fuel Cell Cartridges," filed on Feb. 25, 2005, as well as commonly-owned, co-pending U.S. provisional application Ser. Nos. 60/689,538, entitled "Hydrogen-Generating Fuel Cell Cartridges," and 60/689,539, entitled "Hydrogen-Generating Fuel Cell Cartridges," both of which were filed on Jun. 13, 2005, the internal pressure of fuel supply dictates whether or not additional fuel is produced within the fuel supply. The disclosures of all of the above-listed references are incorporated herein by reference in their entireties. In this case, the internal pressure of the pressure cartridge is preferably monitored with a pressure sensor.

Fuel cell 9 includes several fuel cell units 16 arranged into stacks. Fuel cell units 16 may be any type of fuel cell unit known in the art, as discussed above. Fuel cell units 16 may include at least a PEM sandwiched between an anode layer and a cathode layer. Typically, several sealing layers are also included with fuel cell unit 16. As described above, fuel cell units 16 generate free electrons, i.e., electricity, to power electronic device 11.

With further reference to FIG. 1, fuel supply 12 comprises an outer shell or casing 21 and a nozzle 22. Nozzle 22 houses shut-off valve 24 (shown in FIGS. 2-5), which is in fluid communication with the fuel stored in fuel supply 12. Shut-off valve 24 in turn is connected to pump 14. Suitable shut-off valves 24 are fully disclosed in the '006 patent application. Pump 14 is optional if fuel supply 12 is pressurized; in such a case, pump 14 may be replaced by a valve.

The size and shape of fuel cell housing 17 need only be sufficient to contain fuel cell units 16, pump 14, controller 18, and information storage device 13. Fuel cell housing 17 is also preferably configured to receive fuel cartridge housing 21. Housing 17 is preferably configured such that fuel supply 12 is easily connectable to housing 17 by the consumer/end user. Supply 12 can be formed with or without an inner liner or bladder. Cartridges without liners and related components are disclosed in the '793 patent application. Cartridges with inner liners or bladders are disclosed in the '004 patent application.

Controller 18 is preferably provided within housing 17 to control the functions of electronic device 11, supply 12, pump 14 and fuel cell units 16, among other components. Alternatively, controller 18 may be remotely located from fuel cell system 10 and connected thereto via a communications transmission link, such as a radio frequency link or an optical link. Preferably, housing 17 also supports at least one optional battery 19 for powering various components of system 10 and electronic device 11 when fuel cell 9 is not operating or during system start-up, shut down, or when otherwise necessary. Alternatively, optional battery 19 powers controller 18 when fuel supply 12 is empty or when the fuel cell 9 is off. Optional battery 19 can be replaced by or used in conjunction with solar panels. Additionally, optional battery 19 may be recharged by fuel cell 9 or another appropriate source, such as a wall outlet or solar panels.

In the present invention, a monitoring system is included with fuel cell system 10. Monitoring system includes a plurality of sensors 30 for monitoring one or more parameters of the fuel contained within fuel cell supply 12. In the first embodiment as shown in FIG. 1, plurality of sensors 30 are located on a single sensor chip 28, which is preferably an integrated circuit chip. Preferably, neither plurality of sensors 30 nor sensor chip 28 contain memory; the information gathered by sensors 30 are relayed to controller 18 and could be stored in information storage device 13, which is described in greater detail hereinafter. In an alternate embodiment, however, sensor chip 28 may contain memory similar to information storage device 13.

Typically, several fuel parameters should be monitored. For example, the parameters include but are not limited to pressure, temperature, the presence and levels of dissolved gasses, ion concentrations, fuel density, the presence of impurities, duration of use, stress and strain to which fuel supply is subjected, as well as the amount of fuel remaining within the fuel cartridge. Preferably, at least one of sensors 30 is a pressure sensor. The pressure sensor may be any type of pressure sensor known in the art that is capable of being placed in fuel supply 12 and measuring pressure in the anticipated range of approximately 0-40 psi, although this range may vary depending upon the fuel cell system and fuel used. For example, the pressure sensor may be a pressure transducer available from Honeywell, Inc. of Morristown, N.J. The pressure sensor may also be a glass or silica crystal that behaves like a strain gauge, i.e., the crystal emits a current depending upon the amount of pressure. The pressure sensor may be used alone or in conjunction with other sensors monitoring different aspects of the fuel.

The pressure can also be sensed by a piezoelectric sensor. Piezoelectric sensors are solid state elements that produce an electrical charge when exposed to pressure or to impacts. Changes in pressure inside the fuel supply due to internal pressure or impacts cause a signal to be produced from the sensor, which can be transmitted to the controller for processing or action. Suitable piezoelectric sensors are available from many sources, including PCB Piezotronics. Additionally, the piezoelectric sensor can also be configured to measure a force acting on the fuel supply or on the fuel cell system, and can also act as an accelerometer so that if the fuel supply is dropped the sensor would recognize the acceleration and signals the controller for actions, e.g., shut down or fail-safe operations. The piezoelectric sensors can be located on fuel supply 12, on fuel cell system 10 or on electronic device 11.

The pressure can also be sensed by an optical sensor. The use of passive optical sensors is well known, as discussed, for example, in U.S. Pat. No. 4,368,981, the disclosure of which is incorporated herein in its entirety by reference. As shown in FIG. 1A, fuel cell 9 includes a light source 60, such as a variable wavelength laser, a light emitting diode, or similar source of visible or non-visible radiation. Fuel cell 9 also includes at least one photodetector 64. Both light source 60 and photodetector 64 are linked to controller 18. An optically invisible window 62a is disposed on a surface of housing 17 facing fuel supply 12 so that the aperture of light source 60 is aligned with window 62a. Similarly, a second optically invisible window 62b is disposed on a surface of casing 21 so that when fuel supply 12 is attached to fuel cell 9, window 62a aligns with window 62b. Optically connected to window 62b within fuel supply 12 is at least one sensor 30. One of sensors 30 can be optical sensor 61 which may be any passive optical sensor known in the art, such as an interferometer, a Michelson sensor, a Fabry-Perot sensor and the like. In one embodiment, optical sensor 61 generally includes two coils of optical fiber which initially have the same length. An exposed optical fiber 63a is subjected to environmental conditions within fuel supply 12, while a reference coil of optical fiber 63b is shielded therefrom. In one example, exposed coil 63a is wrapped around a fuel liner and reference coil 63b is positioned inside the fuel liner, on an exterior surface of the outer casing, or between the fuel liner and the outer casing. If the pressure in the fuel liner increases then the liner would increase in volume, thereby stretching the exposed fiber. The difference between the exposed and the reference coils indicates an increase in pressure. Additionally since both fiber coils are at substantially the same temperature, this optical sensor is not sensitive to temperature. In the event that the exposed fiber is broken due to the pressure in the liner, the failure of the light in exposed coil 63a to reach photodetector 64 or optional photodetector 64a may also indicate high pressure.

In operation, light source 60 emits light, preferably a pulse of known duration, which shines through window 62a and into window 62b. The light is optically transferred to both coils 63a, 63b at the same time. The light travels through coils 63a, 63b and is reflected back through windows 62b and 62a. The light signals are detected by photodetector 64. Optionally, photo detector 64 comprises detectors 64a, 64b corresponding to coils 63a and 63b. As pressure increases within fuel supply 12, the length of exposed coil 63a increases relative to the length of reference fiber 63b, causing a slight delay in receiving the signal from coil 63a. From this time delay, the pressure within fuel supply 12 may be calculated by controller 18.

One of sensors 30 may also be a temperature sensor. The temperature sensor can be any type of temperature sensor known in the art, such as a thermocouple, a thermistor, or an optical sensor. Anticipated typical temperatures desired to be monitored range from about −20 to 55 degrees centigrade. A temperature sensor may be used alone or in conjunction with other sensors monitoring different aspects of the fuel. If an optical sensor is used, the type and method of operation thereof is substantially similar to that described above with respect to the pressure within fuel supply 12.

One of sensors 30 may also be a sensor for measuring dissolved gases, such as an oxygen or hydrogen sensor. These dissolved gas sensors may be any type known in the art. For example, one type of appropriate oxygen sensor is a galvanic cell, including an anode and a cathode surrounded by an electrolytic solution. The galvanic cell produces an electric current proportional to the pressure of detected oxygen. The dissolved gas sensor may be used alone or in conjunction with other sensors monitoring different aspects of the fuel.

One of sensors 30 may be a fuel gauge. One type of fuel gauge suitable for use on a chip 28 is a thermistor (or thermister) which can be used to measure the remaining fuel in fuel supply 12. A thermistor is a semi-conducting resistor that is sensitive to temperature changes. In other words, the resistance of the thermistor changes as the temperature changes. Generally, there are two types of thermistors: negative temperature coefficient (NTC) thermistors and positive temperature coefficient (PTC) thermistors. NTC thermistors display a decrease in its resistance when exposed to increasing temperature, and PTC thermistors display an increase in its resistance when exposed to increasing temperature. Thermistors have been traditionally used to measure the temperature of a system or a fluid. The use of thermistors as a fuel gauge is discussed in detail in parent application '236, previously incorporated by reference.

An important aspect of the thermistor's resistance depends on the thermistor's body temperature as a function of the heat transfer inside the fuel cartridge and the heat transfer within the electronic device that the fuel cell powers. Heat transfer occurs mainly by conduction and radiation in this environment or from heating caused by power dissipation within the device. In traditional temperature measuring function, self heating must be compensated so that the accurate temperature can be obtained. In accordance with the present invention, self heating is not compensated so that the capacity to dissipate heat of the remaining fuel inside fuel cartridge can be gauged. The heat capacity is related to the amount of fuel remaining in the cartridge. Both NTC and PTC thermistors are usable with the present invention.

Generally, heat capacitance or heat conductivity is described as the ability of a fluid, i.e., liquid or gas, to conduct or dissipate heat. Liquid, such as water or methanol, has a much higher capacity to dissipate heat than gas, such as air, carbon dioxide or methanol gas. The capacity of a fluid to dissipate heat is equal to its heat capacitance, which is a constant for a particular fluid, multiplied by the fluid volume. Hence, this aspect of the present invention measures the volume of the remaining fuel by measuring the electrical resistance of the thermistor positioned within the fuel or on the optional liner containing the fuel. The electrical resistance is then converted to the capacity of the remaining fuel to dissipate heat, and this capacity is converted to the volume of remaining fuel by dividing out the heat capacitance constant. In other words, higher heat capacity corresponds to higher remaining fuel volume.

The thermistor-fuel gauge should be calibrated prior to use. The operating temperatures of the fuel cell and of the electronic device are known. An electrical signal from a full liner is recorded and then an electrical signal from an empty liner is recorded. One or more signals from known partial volumes can also be recorded. A calibration curve can be drawn from these calibration points between these operating temperatures. A real-time signal is compared to this calibration curve to determine the remaining fuel. Other methods of calibrations can be performed without deviating from the present invention.

Additionally, since the thermistor is a resistor, electrical current that flows through the thermistor generates heat. Therefore, electrical current can flow through the thermistor to generate heat that can be dissipated by the remaining fuel, and accurate readings can be obtained. In one embodiment, controller 18 sends the current as a query to the thermistor to gauge the amount of heat dissipation whenever a remaining fuel reading is desired. The electrical current can be sent intermittently or continuously.

In accordance with another aspect of the present invention, a thermocouple can be used as a fuel gauge. The use of a thermocouple as a fuel gauge is described in detail in parent application '236, previously incorporated by reference. A thermocouple is also typically used to measure temperature and comprises two wires made from different metals, and is also known as a bi-metal sensor. The wires are joined at two junctions. A potential difference is established when a measuring junction is at a temperature that is different than a temperature at a reference junction. The reference junction is typically kept a known temperature, such as the freezing point of water. This potential difference is a DC voltage which is related to the temperature at the measuring junction. Using a thermocouple to measure temperature is well known in the art.

Similar to the thermistor, a thermocouple acts like a resistor that is sensitive to temperature. The thermocouple is capable of measuring the heat capacity of the remaining fuel by measuring the potential difference. Hence, the thermocouple can also measure the remaining fuel. Alternatively, electrical current can be sent through the measuring junction of the thermocouple. The current heats up the measuring junction and the fuel dissipates the heat. The amount of heat dissipated, therefore, relates to the remaining fuel. The current can be sent intermittently or continuously. The thermocouple fuel gauge should be calibrated similar to the calibration of the thermistor, discussed above.

In accordance with another aspect of the present invention, an inductive sensor can be used to measure the remaining fuel. The use of inductive sensors as a fuel gauge is described in detail in parent application '236, previously incorporated by reference. Inductive sensors are typically used as on/off proximity switches. An inductive sensor contains a wire coil and a ferrite core, which form the inductive portion of an inductive/capacitance (LC) tuned circuit. This circuit drives an oscillator, which in turn generates a symmetrical, oscillating magnetic field. When an electrical conductor, such as a metal plate, enters this oscillating field, eddy currents are formed in the conductor. These eddy currents draw energy from the magnetic field. The changes in the energy correlate to the distance between the inductive sensor and the electrical conductor.

One of sensors 30 may also be a clock or other form of timing or counting mechanism. Examples of the timing mechanism may include an oscillator, such as a crystal or induction oscillator, integrated onto chip 28. As the counter relies upon memory such as information storage device 13, which is preferably housed in fuel cell 9, the counter counts the oscillations only when fuel supply 12 is connected to fuel cell 9. In this way, the counter may track how long fuel supply 12 has been in use. The count of oscillations is preferably stored in information storage device 13. The oscillator can be powered by an optional battery internal to fuel supply 12 or may be triggered by power transferred from fuel cell 9, such as when pump 14 is turned on. If information storage device 13 also tracks pumping rates, controller 18 may be programmed to calculate flow rate of fuel through pump 12 and, consequently, the remaining fuel in fuel supply 12. In other words, the combination of a counter and tracking of pumping rates may be used as a fuel gauge.

Alternatively, the timing mechanism may include an energy storage device with a known decaying signature housed in fuel supply 12. For example, fuel supply 12 could include a battery whose self-discharge rates are known and a battery tester may be incorporated into fuel cell 9. It is known in the art that a typical nickel-based battery discharges approximately 10-15% of its charge in the first 24 hours after the charge is maximized, followed by additional 10-15% losses monthly thereafter. Similarly, it is known that lithium ion batteries self-discharge about 5% in the first 24 hours after charge and 1-2% monthly thereafter. Additional information regarding the self-discharge of batteries and monitoring devices therefor can be found in Isidor Buchmann, *The Secrets of Battery Runtime* (April 2001) available on <http://www.batteryuniversity.com/parttwo-31.htm>, the disclosure of which is incorporated herein by reference. By programming controller 18 and information storage device 13 with the self-discharge curves of batteries that are always fully charged when installed in or on fuel supply 12, controller 18 can calculate the age or shelf life of fuel supply 12 based on the measured charge level of the battery at any point in time after fuel supply 12 is attached to fuel cell 9.

Additionally, the monitoring system should be robust. Fuels, in general, may have degrading effects on materials exposed to the fuel, and in accordance with one aspect of the present invention materials for the manufacture of fuel supply 12 and its components are selected to be compatible with fuels. Chip 28 and/or sensors 30 may be placed in contact with the fuel, such as floated in the fuel or affixed to an inner surface of casing 21 or the optional liner. Therefore, the monitoring system should be able to withstand sustained contact with the fuels used in fuel cells.

A suitable protective material is silicon dioxide ($SiO_2$), which can be applied by vapor deposition or sputtering technique or other known methods. Silica molecules coalesce on a substrate as $SiO_x$ where x is 1 or 2. Any protective material that can be suspended in a solvent can be used.

Other suitable coatings include, but are not limited to, the class of epoxy-amine coatings. Such coatings are commercially available as Bairocade® coatings from PPG Industries, Inc. of Cleveland, Ohio. These types of coatings can be applied using electro-static guns and cured in infrared ovens to create the gas barrier. The coatings can also be applied by dipping, spraying or painting. These coatings are typically used to coat beverage bottles or cans to protect the beverages inside.

Additionally, a clear polycrystalline, amorphous linear xylylene polymer may coat and protect the sensor. Xylylene polymer is commercially available as Parylene® from Cookson Specialty Coating Systems of Indianapolis, Ind. Three suitable Parylene resins are Parylene N (poly-para-xylylene), Parylene C (poly-monochloro-para-xylylene) and Parylene D (poly-dichloro-para-xylylene). Additional discussion of Parylene can be found in co-owned, co-pending U.S. patent application Ser. No. 10/913,715, entitled "Fuel Supplies for Fuel Cells," filed on Aug. 6, 2004, the disclosure of which is hereby incorporated by reference herein in its entirety.

In accordance with another aspect of the present invention, a gas barrier film is wrapped around sensors 30 for protection. Suitable gas barrier films include Mylar® from DuPont and various films from the food packaging industry. More detailed information regarding gas barrier films, including a list of appropriate films, may be found in the '715 application, previously incorporated by reference. Other appropriate materials include polyvinyl alcohol (PVOH), ethylene vinyl alcohol (EVOH), EVOH bonded to a polyester substrate, polyvinylidene chloride copolymers (PVDC or Saran), nylon resins, fluoro-polymers, polyacrylonitrile (PAN), polyethylene naphthalate (PEN), poly(trimethlylene terephthalate) (PTT), resorcinol copolymers, liquid crystal polymers, aliphatic polyketones (PK), polyurethane, polyimide, and blends and copolymers of these materials.

Furthermore, sensor 30 may be protected from the fuel by virtue of being placed within housing 21 but outside of a bladder or liner, such as liner 27 as shown in FIG. 2 and discussed in greater detail below. Additional protective coatings and protective films suitable for the sensors are disclosed in the '715 patent application.

Referring again to FIG. 1, as chip 28 and information storage device 13 are preferably located remote from one another, controller 18 initiates the gathering of information from sensors 30, for example, when fuel supply 12 is first inserted into fuel cell 9. Controller 18 can transmit a signal and/or power to chip 28 to interrogate the sensors 30. Sensors 30 then take readings which are preferably passed back to controller 18. The communication between controller 18 and chip 28 takes place via a link that, in this embodiment, is hard-wired. Leads 70, preferably electrical wires, are connected to chip 28 and electrical contacts 15A, which are disposed on an exterior face of casing 21. Leads 72, also preferably electrical wires, are connected to controller 18 and electrical contacts 15B. As will be apparent to those in the art, leads 70, 72 and contacts 15A, 15B may be any leads or electrical contacts known in the art.

Electrical contacts 15A and 15B are configured and located such that an electrical connection is established between controller 18 and chip 28 if fuel supply 12 is properly inserted into housing 17. To that end, fuel supply 12 and housing 17 are preferably configured such that fuel supply 12 may only be inserted into housing 17 in the proper position. For example, housing 17 may include tabs that protrude into the cavity for receiving fuel supply 12, and fuel supply 12 may include coordinating slots into which the tabs may slide. Another example would be if the perimeter of the cavity on housing 17 for receiving fuel supply 12 is of an asymmetrical shape and fuel supply 12 has the same shape. Additional ways to insure proper positioning of fuel supply within housing 17 are discussed in commonly owned, co-pending U.S. application Ser. No. 10/773,481, entitled "Datum Based Interchangeable Fuel Cell Cartridges," filed on Feb. 6, 2004, the disclosure of which is hereby incorporated herein by reference in its entirety.

In other embodiments, the communication link between sensors 30 and controller 18 is a wireless system that is capable of transmitting electrical signals. Suitable wireless transmission systems include any wireless transmission systems known in the art, including, inter alia, Blue Tooth technology, radio frequency, infrared rays, and light transmissions such as from lasers or LEDs from the fuel cell 9 side to photonic sensors on fuel supply 12. Such wireless transmissions can also transmit or transfer power to sensors 30.

As described in the parent '237 application, the fuel supply may include an information storage device that possesses an ability to store information such as fuel content including fuel content during usage, fuel quantity, fuel type, anti-counterfeit information, expiration dates based on age, manufacturing information and to receive information such as length of service, number of refuels, and expiration dates based on usage.

Information relating the conditions of the fuel may change over time, and it is useful to monitor and store such information. However, the conditions of the fuel, e.g., viscosity as a function of temperature discussed above, can change from the time electronic device 11 is turned off until it is turned on again, e.g., between nighttime and daytime. Hence the information stored on a memory device when the device is turned off may be staled when the device is turned on again. Hence, in certain circumstances it is desirable to interrogate sensors 30 instead of reading the information stored on information storage device 13. Stored information includes protectable information and rewriteable information.

Protectable information, which cannot be easily erased, includes, but is not limited to, type of cartridge; date the cartridge was manufactured; lot number for the cartridge; sequential identification number assigned to the cartridge during manufacturer; date the information storage device was manufactured; lot number for the information storage device; sequential identification number assigned to the information storage device; machine identification number for the cartridge and/or storage device; shift (i.e., time of day) during which the cartridge and/or storage device were produced; country where the cartridge and/or storage device were produced; facility code identifying the factory where the cartridge and/or storage device were produced; operating limits, including but not limited to temperature, pressure, vibration tolerance, etc.; materials used in manufacturing, anti-counterfeit information; fuel information; such as chemical formulation; concentration; volume; etc.; intellectual property information, including patent numbers and registered trademarks; safety information; security password or identification); expiration date based on date of manufacturing; shutdown sequence; hot swap procedure; recycling information; reactant information; fuel gage type; new software to update fuel cell 9 and/or controller 18; and fluid sensor information.

Rewriteable information includes, but is not limited to, current fuel level and/or current ion level in the fuel; number of ejections/separations of the cartridge from the electrical device and/or fuel cell or number of times that the cartridge was refilled; fuel level on ejection/separation of the cartridge from the electrical device and/or fuel cell; number of insertions/connections of the cartridge to the electrical device and/or fuel cell; fluid level on insertion/connection of the cartridge to the electrical device and/or fuel cell; current operation status including rate of power consumption; acceptance/rejection of a particular electronic device; maintenance status and marketing information for future cartridge designs; triggering events; expiration date based on actual usage; efficiency of the system; operational history of the fuel cell system; such as temperatures and pressures during selected time periods (e.g., at start-ups and shut-downs or periodically); and operational history of the electronic devices, such as number of digital pictures per cartridge, maximum torque for power tools, talking minutes and standby minutes for cell phones, number of address look-ups per cartridge for PDAs, etc.

Information storage device 13 is preferably an electrical storage device, such as an EEPROM memory chip as discussed and disclosed in the parent '237 application, previously incorporated by reference. Suitable information storage devices include, but are not limited to, random access memory (RAM), read-only memory (ROM), programmable read-only memory (PROM), erasable programmable read-only memory (EPROM), electrically erasable programmable read-only memory (EEPROM), flash memory, electronically readable elements (such as resistors, capacitance, inductors, diodes and transistors), optically readable elements (such as bar codes), magnetically readable elements (such as magnetic strips), integrated circuits (IC chips) and programmable logic arrays (PLA), among others. The preferred information storage device includes PLA and EEPROM, and the present invention is described herein with the EEPROM. However, it is understood that the present invention is not limited to any particular type of information storage device.

Preferably, information storage device 13 generally has a substrate (not shown) formed of a "potting material," an integrated circuit memory chip (not shown), and etched or printed layers or strips of electrical circuitry or contacts (not shown). The integrated circuit memory chip (not shown) can be connected to the substrate (not shown) with a plurality of pins, such as in an external electronic connector.

Information storage device 13 is preferably connected to controller 18 via link 25, preferably an electrical connection. Alternatively, link 25 is a wireless system that is capable of transmitting electrical signals between information storage device 13 and controller 18. Suitable wireless transmission systems include any wireless transmission systems known in the art, such as Blue Tooth technology, radio frequency, infrared rays, optical transmissions, etc.

Information storage device 13 can have any particular memory size. The memory size is determined by the amount of data needed to be stored. Suitable memory size typically ranges from about 128 bytes to about 512 K bytes. Memory sizes of 1 M bytes and higher are also commercially available and are usable in the present invention. Information storage device 13 is also not limited to any particular dimensions so long that it can fit within housing 17 of fuel cell 9.

Information storage device 13 preferably includes portions 13*a* and 13*b*. Portion 13*a* is pre-programmed or set up by the manufacturer to include read-only (write protected or protectable) data, discussed above. Controller 18 can read the data in portion 13*a* of information storage device 13. However, the controller 18 cannot modify or erase the read-only data in portion 13*a*. Portion 13*b* is programmed or set up by the manufacturer to include rewriteable data, discussed above. Controller 18 can read and write/erase the data in portion 13*b*. Portions 13*a* and 13*b* are electrically connected to link 25 via conventional electrical wires or printed circuit boards, etc., known by those of ordinary skill in the art or by the wireless connections listed above.

A second embodiment of the present invention is shown in FIG. 2. In this embodiment, which is similar to the first embodiment shown and described with respect to FIG. 1, plurality of sensors 30 is not contained on a chip, but is preferably distributed throughout fuel supply 12. Fuel supply 12 preferably includes a liner 27.

In this embodiment, a fuel gauge may comprise two sensors placed within or on fuel supply 12. The first sensor should be placed on a location that moves as the fuel is removed to reflect the level of fuel remaining in the cartridge. For example, the first sensor can be placed directly on liner 27. The second sensor is positioned outside of fuel supply 12, e.g., on fuel cell 9 or electronic device 11. The second sensor is electrically connected to either fuel cell 9 or to electronic device 11. An electrical circuit connected to the second sensor can measure electrical or magnetic properties between these sensors, which correlate or are related to the fuel level. The electrical circuit can also be connected to the first sensor via an electrical wire extending through the wall of fuel supply 12. This type of fuel gauge is more completely described in the '236 parent application.

The information collected from sensors 30 may be used in a variety of ways. For example, if the temperature of the fuel falls, then the fuel becomes more viscous and, therefore, harder to pump. Controller 18 may dynamically regulate valve 24 so that sufficient fuel may be pumped to system 10. Further, by monitoring the heat cycles to which the fuel is subjected, controller 18 may be programmed to extrapolate the amount of fuel remaining in fuel supply 12 and produce a fuel gauge read out.

As will be recognized by those in the art, the placement of sensors 30 on or near fuel supply 12 could have many configurations. For example, sensor chip 28 may be separable from fuel supply 12. Fuel supply 12 includes at least one port for the transfer of fuel, such as the port closed by shut-off valve 24. One of these ports could be adapted so that a pod containing sensor chip 28 could be removably inserted therein. In a case where sensors 30 do not need to be in direct contact with the fuel, such as, for example, if monitoring temperature by contact with a bladder or liner within fuel supply 12, an access port for a sensor pod could be placed anywhere on fuel supply 12. Additionally, sensors 30 could be located within housing 17 of fuel cell 9. In such a case, the connection of electrical contacts 15B and 15A (shown in FIG. 1) upon insertion of fuel supply 12 into housing 17 provides sensors 30 access to the fuel within fuel supply 12 for monitoring.

Figure 3:
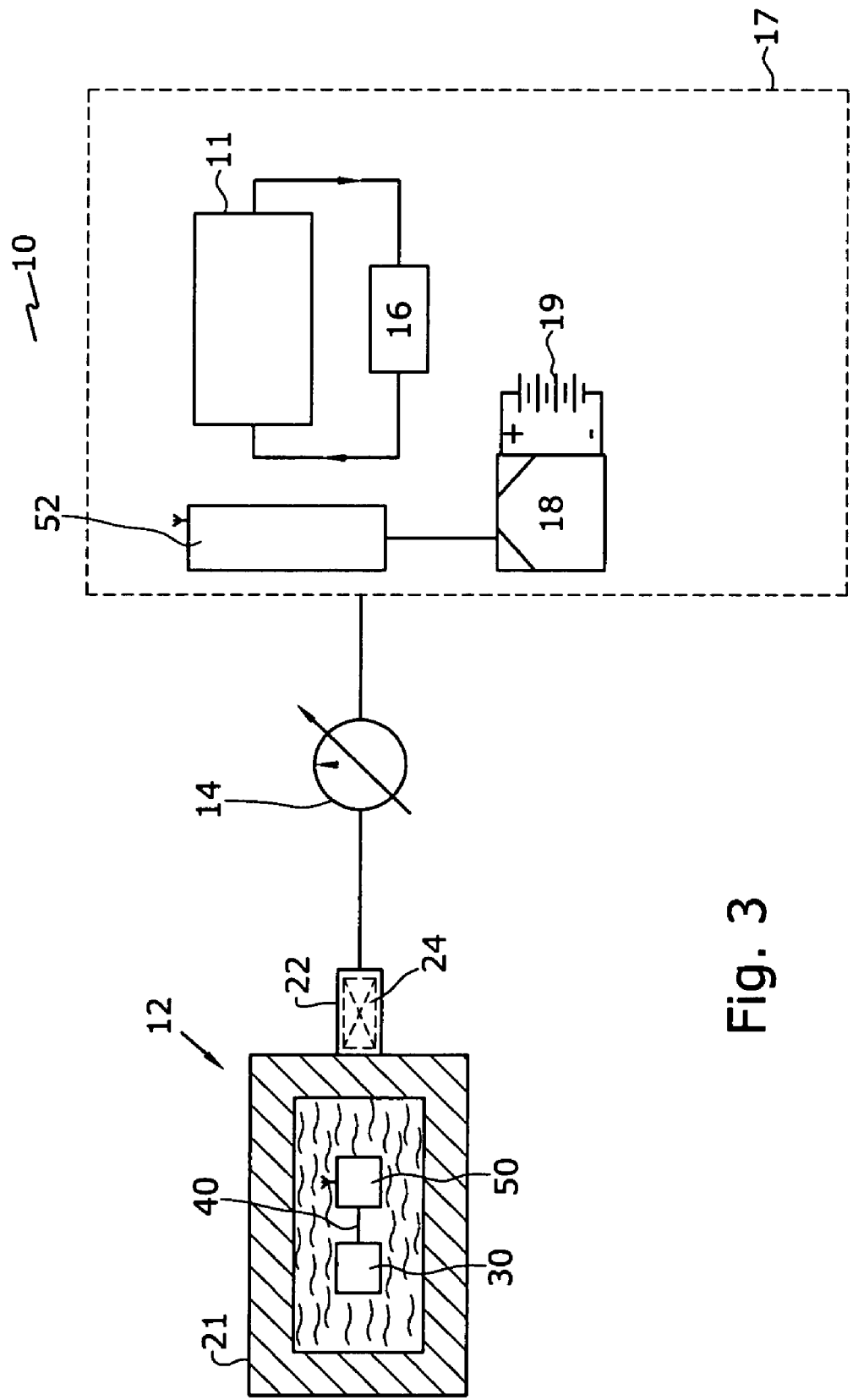
FIG. 3 is a schematic view of a fuel cell system according to the present invention, wherein a monitoring system in a fuel cartridge is remotely linked to a controller and information storage device.
Figure 4:
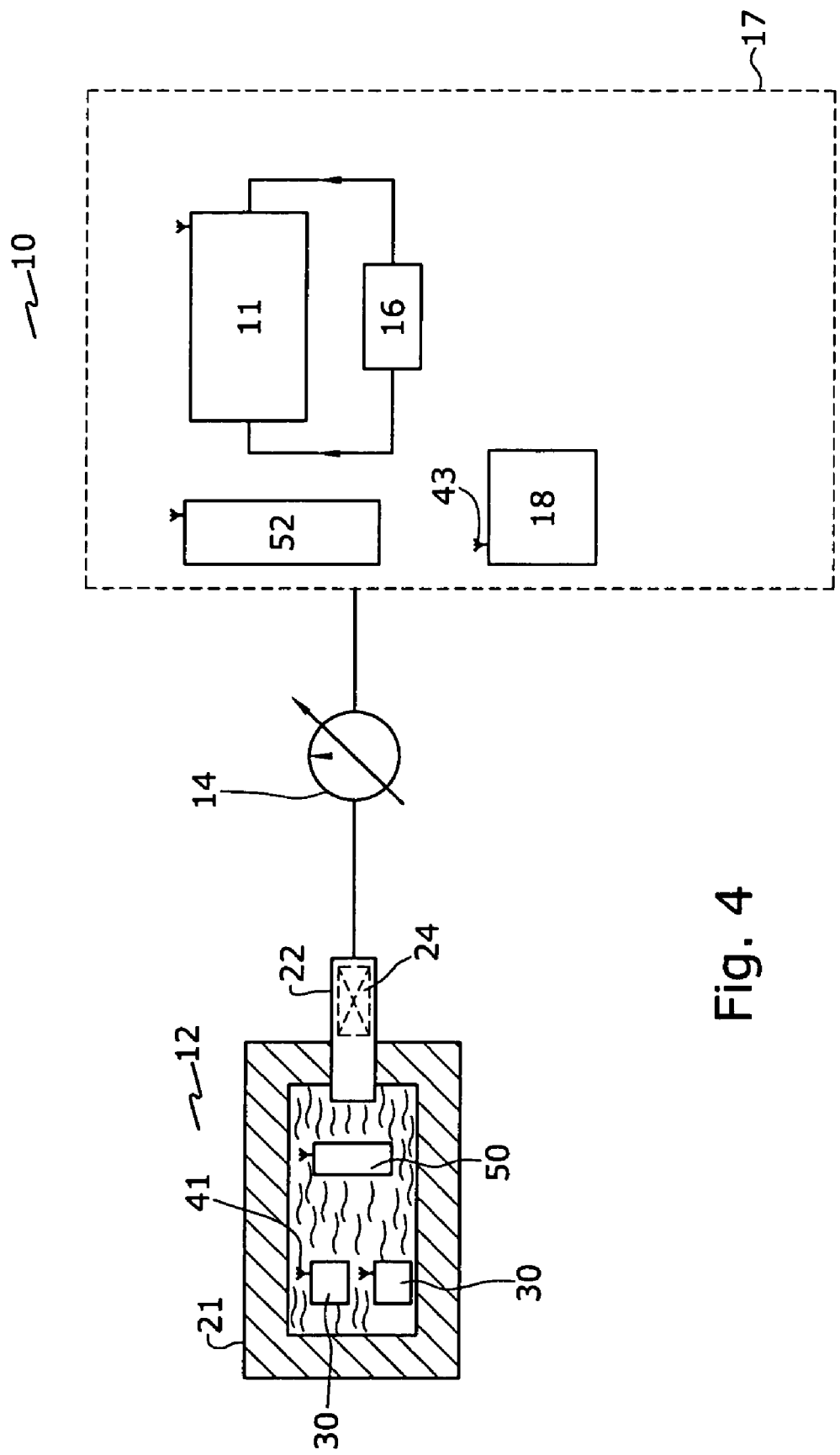
FIG. 4 is a schematic view of a second embodiment of the fuel cell system of the present invention, wherein sensors of the monitoring system are remotely linked to an RFID tag.
Figure 5:
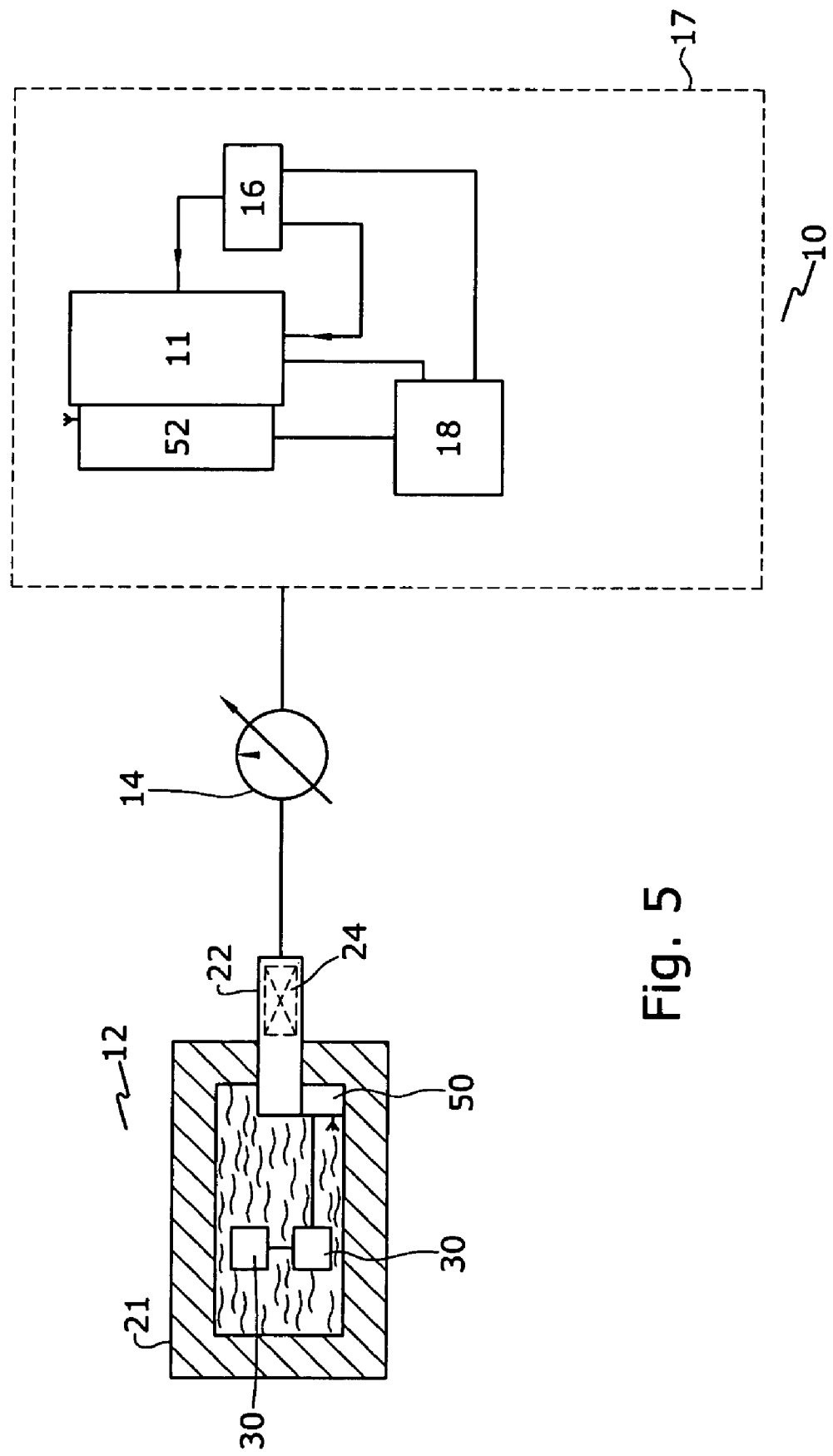
FIG. 5 is a schematic view of a fuel cell system according to a third embodiment of the present invention, wherein the RFID tag is fixedly attached to an interior surface of the fuel cartridge.

In yet another embodiment of the present invention as shown in FIGS. 3-5, the monitoring system may also include a radio frequency identification (RFID) tag 50 and an RFID tag reader station 52. RFID tag 50 may be any RFID tag known in the art. RFID tag 50 may be passive or active. If RFID tag 50 is active, a power source, such as a battery, is also required. Generally, RFID tags include memory, either read-only or read-write, and a radio frequency transmitter. However, some RFID tags contain no memory, such as read-only RFID tags that include hardwired identification circuits. The structure and operation of RFID tags are more fully described in several U.S. patents, including U.S. Pat. Nos. 4,274,083 and 4,654,658, the disclosures of which are incorporated herein by reference. Suitable RFID tags are commercially available from many sources, including Philips Semiconductors of San Jose, Calif., among others.

RFID tag 50 preferably includes sufficient read-write memory to contain the data collected from the sensors (described below), although RFID tag may also be linked via electrical connection to a separate information storage device located on fuel cell 9.

RFID tag 50 may be located anywhere on or within fuel supply 12, for example on the top, bottom, or sides of the exterior surface of the outer casing 21. In the embodiment shown in FIGS. 2, 3, and 4, RFID tag(s) 50 is disposed within fuel supply 12, i.e., RFID tag 50 is floated within the fuel. Alternatively, as shown in the embodiment shown in FIG. 5, RFID tag 50 is adhered to an interior surface of fuel supply 12 such as by gluing or welding.

RFID tag 50 communicates with RFID reader station 52. RFID reader station 52 emits a radio frequency signal that communicates with RFID tag 50 and, in the case of passive RFID tags, powers RFID tag 50 by induction. As shown in FIGS. 3, 4 and 5, RFID reader station 52 is preferably located in the body of system 10 separate from fuel supply 12. Alternatively, as shown in FIG. 5, RFID reader station 52 may be disposed on or within electronic device 11 to which system 10 is providing power. RFID reader station 52 may also be a handheld device or located on an external surface of fuel supply 12. RFID reader station 52 is also linked, either directly via a hardwired link or indirectly via a transmitted signal, to controller 18. Controller 18 thereby triggers an interrogation by RFID reader station 52 and also receives the information transmitted to RFID reader station 52 from RFID tag 50.

In both of these embodiments, RFID tag 50 should be protected from possible reaction with the fuel. Preferably, RFID tag 50 may be enclosed or encased in a material that is inert to the fuel. "Inert", as used in this context, refers to the ability of the material to withstand lengthy exposure to a fuel such as methanol. For example, RFD) tag 50 may be potted within the same material used to form outer casing 21. RFID tag 50 may also be contained within a shell, such as a plastic or metal capsule, as long as the material chosen for the capsule does not significantly interfere with the radio frequency signals transmitted or received by RFID tag 50. Additionally, RFID tag 50 may be coated with any of the coating materials described above with respect to sensor(s) 30, such as xylylene.

Figure 6:
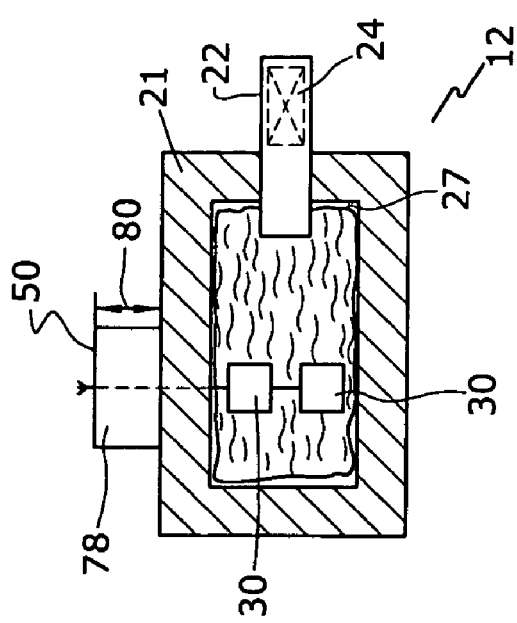
FIG. 6 is a schematic view of a fuel supply according to the present invention having an RFID tag affixed to an outer surface thereof.

In another embodiment, shown in FIG. 6, fuel supply 12 includes an outer casing 21 made of a metal, such as stainless steel, and fuel contained in a liner 27, similar to the embodiment described above with respect to FIG. 2. In this embodiment, RFID tag 50 is preferably elevated away from the surface of outer casing 21 of fuel supply 12 by a mount 78, as outer casing 21 itself may interfere with the induction process that occurs when RFID reader station 52 is placed in proximity with RFID tag 50. As such, RFID tag 50 is preferably spaced away from the surface of outer casing 21, preferably about 5 mm. The actual distance 80, or height of mount 78, between RFID tag 50 and outer casing 21 depends on many factors, including, inter alia, the operating range requirements of the system, i.e., the anticipated distance between RFID tag 50 and RFID tag reader station 52, the size of RFID tag 50, and the tuning of RFID tag 50 and RFID tag reader station 52. Mount 78 may be made of any material, such as plastic, ceramic, or the like. Mount 78 is preferably affixed to both outer casing 21 and RFID tag 50 using any method known in the art, such as adhering, such as with an adhesive or similar bonding agent, or by press-fitting mount 78 into a recess formed within outer casing 21. Alternatively, mount 78 can be an air gap.

Figure 7:
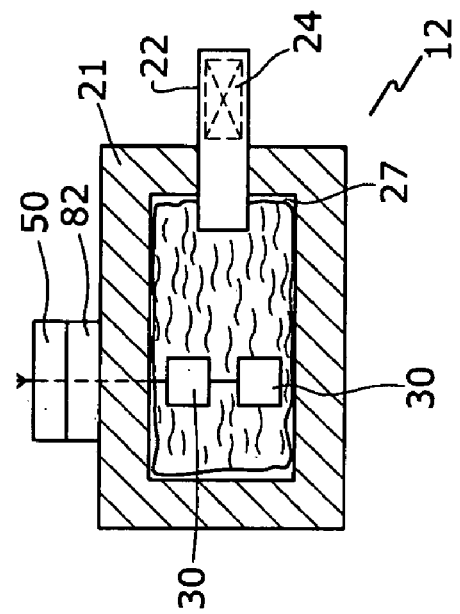
FIG. 7 is a schematic view of a fuel supply according to the present invention having an RFID tag affixed to an outer surface thereof with an insulating materials.

In addition to spacing RFID tag 50 and outer casing 21 apart, other ways of compensating for the interference of a metal outer casing 21 could be used. For example, as shown in FIG. 7, an insulating material 82 may be placed between outer casing 21 and RD tag 50. Preferably, insulating material 82 is a ferrite ceramic material, as the strong magnetic properties of the ferrite shield RFID tag 50 from outer casing 21. Additional ways to overcome the interference of metal outer casing 21 include increasing the strength of the reader field generated by RFID tag reader station 52 and selecting the relative sizes of the of the RFID tag and RFID tag reader station coils.

Sensors 30 may be directly or indirectly linked to RFID tag 50. As shown in FIG. 3, a direct link 40 in this embodiment is an electrical connection that conveys the data produced by sensor 30 to memory on RFID tag 50. In other words, sensor 30 and RFID tag 50 may be incorporated into one chip prior to insertion into fuel supply 12. Alternatively, as shown in FIG. 4, sensor 30 may itself include a radio frequency transmitter 41 that modulates and transmits a signal to either RFID tag 50 or to controller 18, which also includes a radio frequency transceiver 43. Sensor 30 may also be integrated with RFID tag 50 within the same material to form an RFID package. FIG. 5 shows an embodiment where sensors 30 are hardwired to RFID tag 50, which is adhered to an interior surface of casing 21. It will be recognized that RFID tag 50 may also be located on an exterior surface of casing 21.

Additionally, RFID tag 50 may be used to upload new software to fuel cell 9. For example, updated software for controller 18 may be stored in the memory of RFID tag 50. Upon insertion into housing 17, the new software may be transferred to controller 18 via any of the described communication links. As will be recognized by those in the art, other types of information could be stored in the memory of RFID tag 50, such as product recall alerts, new or updated calibration data, and the like.

While it is apparent that the illustrative embodiments of the invention disclosed herein fulfill the objectives of the present invention, it is appreciated that numerous modifications and other embodiments may be devised by those skilled in the art. For example, the fuel cell may be integrated into load 11. Also, pump 14 may be eliminated if pressurized fuel supply configurations are used, such as those described in United States patent publication no. 2005/0074643, the disclosure of which is incorporated herein by reference in its entirety. Additionally, feature(s) and/or element(s) from any embodiment may be used singly or in combination with feature(s) and/or element(s) from other embodiment(s). Therefore, it will be understood that the appended claims are intended to cover all such modifications and embodiments, which would come within the spirit and scope of the present invention.

The invention claimed is:

1. A monitoring system for a fuel cell system comprising:
   a fuel cell having a controller;
   a fuel supply coupled to the fuel cell, wherein the fuel supply contains primarily fuel cell fuel;
   a plurality of sensors operatively connected to the fuel supply; and
   a sensor communication link connecting the sensors and the controller.

2. The system of claim 1 further comprising an information storage device operatively connected to either or both the fuel cell and the controller.

3. The system of claim 2 further comprising an information communication link connecting the controller and the information storage device.

4. The system of claim 2, wherein the information storage device comprises a memory chip or an EEPROM.

5. The system of claim 2, wherein the information storage device comprises an RFID tag, and further comprising an RFID reader station, wherein the RFID reader station is disposed in proximity to the RFID tag.

6. The system of claim 5, wherein at least one of the plurality of sensors transmits data to the RFID tag.

7. The system of claim 6, wherein the sensor is hardwired to the RFID tag to form a RFID package.

8. The system of claim 7, wherein the RFID package is suspended within the fuel.

9. The system of claim 7, wherein the RFID package is disposed on a surface of the fuel supply.

10. The system of claim 5, wherein the RFID tag is operatively coupled to additional memory for storing the data.

11. The system of claim 5, wherein the RFID tag is encased in a material inert to a fuel.

12. The system of claim 11, wherein the material comprises at least one of silicone oxide, xylylene, polyethylene terephthalate, silicon coated polyethylene terephthalatepolyvinyl alcohol (PVOH), ethylene vinyl alcohol (EVOH), EVOH bonded to a polyester substrate, polyvinylidene chloride copolymers (PVDC or Saran), nylon resins, fluoro-polymers, polyacrylonitrile (PAN), polyethylene naphthalate (PEN), poly(trimethlylene terephthalate) (PTT), resorcinol copolymers, liquid crystal polymers, aliphatic polyketones (PK), polyurethane, polyimide, and blends and copolymers of these materials.

13. The system of claim 5, wherein the RFID tag reader station is disposed on the fuel supply.

14. The system of claim 5, wherein the RFID tag reader station is disposed on the fuel cell.

15. The system of claim 1, wherein the sensor communication link comprises an electrical conduit, an RF transmission, magnetic induction, or combinations thereof.

16. The system of claim 1, wherein the plurality of sensors comprises a pressure sensor, a temperature sensor, a timing circuit, a strain gauge, a fuel gauge, a piezoelectric sensor, force sensor, an accelerometer, or combinations thereof.

17. The system of claim 16, wherein the fuel gauge comprises a thermistor, a thermocouple, an inductive sensor, or combinations thereof.

18. The system of claim 1, wherein the sensors are located on a chip.

19. The system of claim 1, wherein the sensors are removably insertable into the fuel supply.

20. The system of claim 1, wherein the sensors are located within or on a fuel supply housing.

21. The system of claim 1, further comprising
a light source operatively connected to the controller; and
at least one photodetector operatively connected to the controller, wherein the plurality of sensors are optical sensors.

22. The system of claim 21, wherein the optical sensors comprise interferometers, Michelson sensors, Fabry-Perot sensors, or combinations thereof.

23. A fuel supply for a fuel cell comprising:
a container, wherein the container contains primarily fuel cell fuel;
at least one sensor for monitoring a condition of the fuel; and
an RFID tag, wherein the RFID tag is configured to communicate with the sensor and be interrogated by an RFID reader station.

24. The fuel supply of claim 23, wherein the RFID tag is operatively coupled to additional memory for storing the data.

25. The fuel supply of claim 23, wherein the RFID tag is encased in a material inert to the fuel.

26. The fuel supply of claim 25, wherein the material comprises wherein the material comprises silicone oxide, xylylene, polyethylene terephthalate, silicon coated polyethylene terephthalatepolyvinyl alcohol (PVOH), ethylene vinyl alcohol (EVOH), EVOH bonded to a polyester substrate, polyvinylidene chloride copolymers (PVDC or Saran), nylon resins, fluoro-polymers, polyacrylonitrile (PAN), polyethylene naphthalate (PEN), poly(trimethlylene terephthalate) (PTT), resorcinol copolymers, liquid crystal polymers, aliphatic polyketones (PK), polyurethane, polyimide, or blends and copolymers of these materials.

27. The fuel supply of claim 23, wherein the RFID tag is suspended within the fuel.

28. The fuel supply of claim 23, wherein the RFID tag is affixed to a surface of the container.

29. The fuel supply of claim 23, wherein the container comprises a metal material.

30. The fuel supply of claim 29, wherein the RFID tag is separated from the surface of the container by a minimum distance.

31. The fuel supply of claim 30, wherein the minimum distance is about 5 mm.

32. The fuel supply of claim 29, wherein the RFID tag is separated from the surface of the container by an insulating material.

33. The fuel supply of claim 32, wherein the insulating material comprises ferrite.

34. A method for monitoring a condition of a fuel supply comprising the steps of:
(i) providing a fuel supply primarily containing a fuel cell fuel; and
(ii) collecting data regarding at least one condition of the fuel supply using a plurality of sensors.
(iii) relaying the information from the sensor to a controller; and
(iv) storing the information in an information storage device, wherein the plurality of sensors is located in the fuel supply and the information storage device is located remotely from the fuel supply.

35. The method of claim 34, wherein step (ii) further comprises collecting information from an RFID tag operatively connected to at least one sensor.

36. The method of claim 35 further comprising the steps of
(v) interrogating the RFID tag; and
(vi) transferring data from the RFID tag to the controller.

37. The method of claim 36, wherein the transferring of data in step (vi) occurs upon intial connection of the fuel supply and the controller.

38. The method of claim 36, wherein the data is software.

39. The method of claim 36, wherein the data comprises calibration tables.

40. The method of claim 34, further comprising the steps of
(v) interrogating the plurality of sensors;
(vi) comparing the data collected from the plurality of sensors to control data; and
(vii) altering a system parameter based upon differences between the collected data and the control data.

41. The method of claim 40, wherein the system parameter comprises a fuel pumping rate, a state of a bleed-off valve, a fuel level monitor, or combinations thereof.

* * * * *